United States Patent [19]

LoJacono et al.

[11] Patent Number: 4,702,448
[45] Date of Patent: Oct. 27, 1987

[54] SUPPORT BRACKET

[76] Inventors: Francis X. LoJacono, 26 Balboa Coves, Newport Beach, Calif. 92663; Janet S. Roberts, 15927 Wicklow La., Huntington Beach, Calif. 92647

[21] Appl. No.: 825,313

[22] Filed: Feb. 3, 1986

[51] Int. Cl.$^4$ .............................................. A47B 96/06
[52] U.S. Cl. .............................. 248/231.7; 248/225.31; 248/230; 248/316.1; 269/249
[58] Field of Search ................ 248/231.7, 231.1, 231.2, 248/225.31, 218.4, 219.3, 316.1, 154, 230; 24/460, 525; 5/503; 74/89.15; 269/45, 76, 77, 249

[56] References Cited

U.S. PATENT DOCUMENTS

| | | | |
|---|---|---|---|
| 2,879,962 | 3/1959 | Biskup | 248/225.31 X |
| 2,905,423 | 9/1959 | Smith et al. | 248/231.7 |
| 3,425,127 | 2/1969 | Long et al. | 248/230 X |
| 3,902,931 | 9/1975 | Dancinger et al. | 248/231.7 X |
| 3,949,880 | 4/1976 | Fortunato | 248/231.7 X |
| 3,991,961 | 11/1976 | Platzer | 248/231.7 X |
| 4,576,057 | 3/1986 | Saari | 74/89.15 X |

Primary Examiner—Ramon O. Ramirez
Attorney, Agent, or Firm—Francis X. LoJacono

[57] ABSTRACT

An adjustable support-and-suspension bracket designed particularly for use with a mounting structure, such as an I.V. pole system, wherein the bracket is defined by a clamp body having a head portion, an opening to receive a mounting structure, and a clamping device disposed within the body. There is attached to the head portion a pair of oppositely positioned support arms which extend outwardly therefrom to allow various devices to be supported or suspended. The clamping device comprises a threaded stud having a knob on one end thereof, the threaded stud being rotatably mounted in a housing formed in the clamp body. A threaded clamping sleeve is mounted to the threaded stud for longitudinal movement as the stud is rotated. When the threaded stud is rotated in the proper direction, the clamping sleeve is extended so that the mounting structure is tightly clamped within the body opening.

21 Claims, 8 Drawing Figures

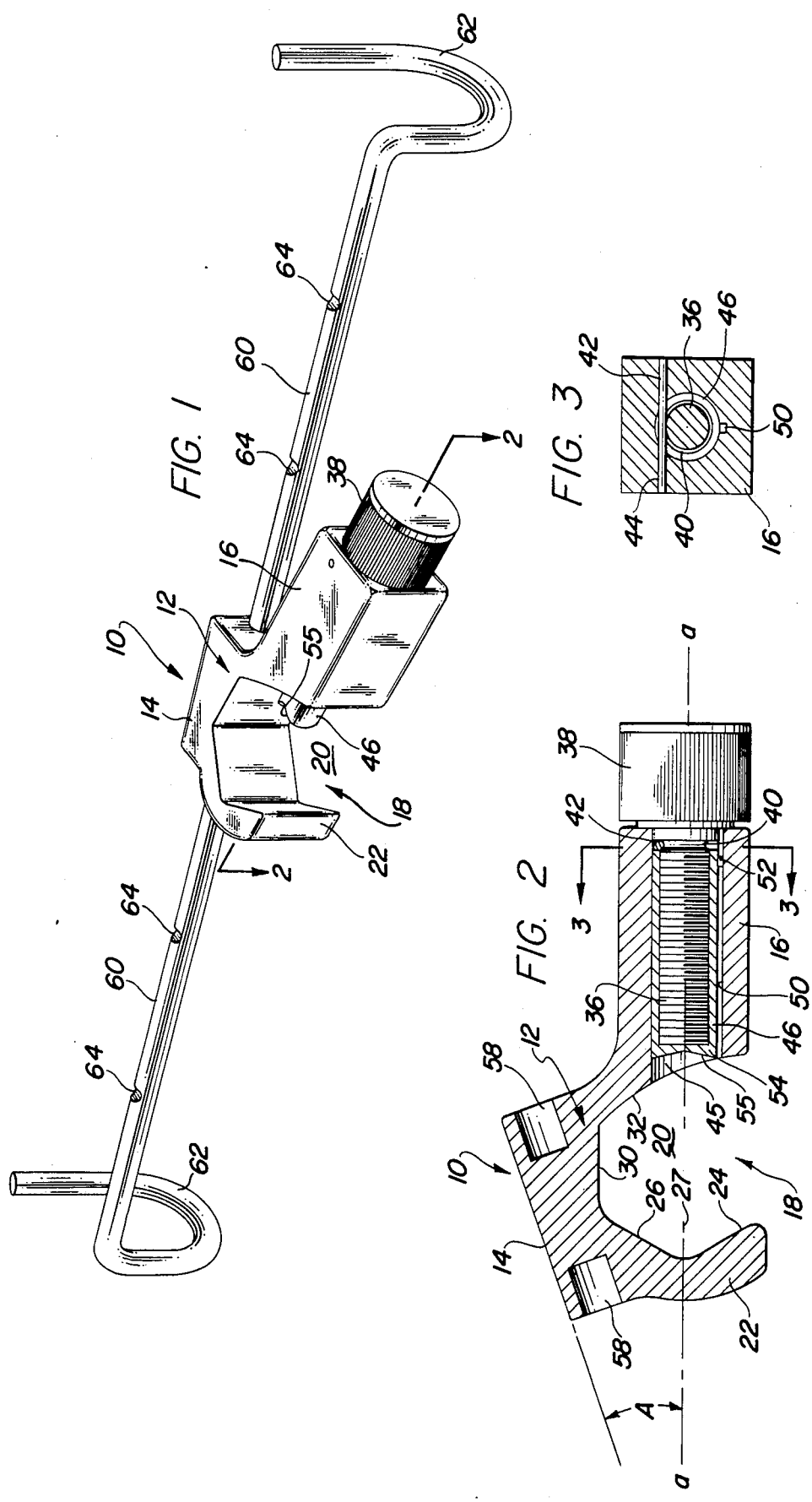

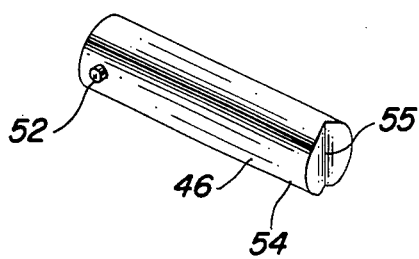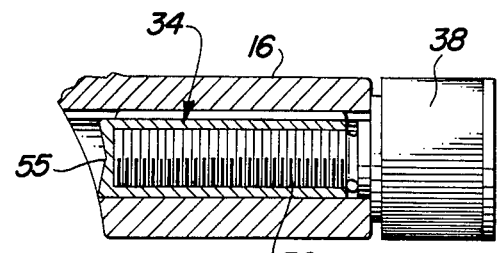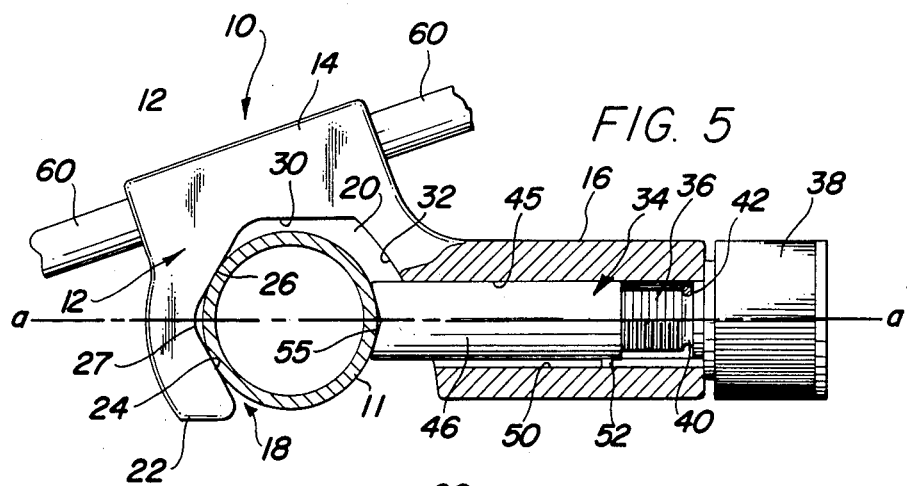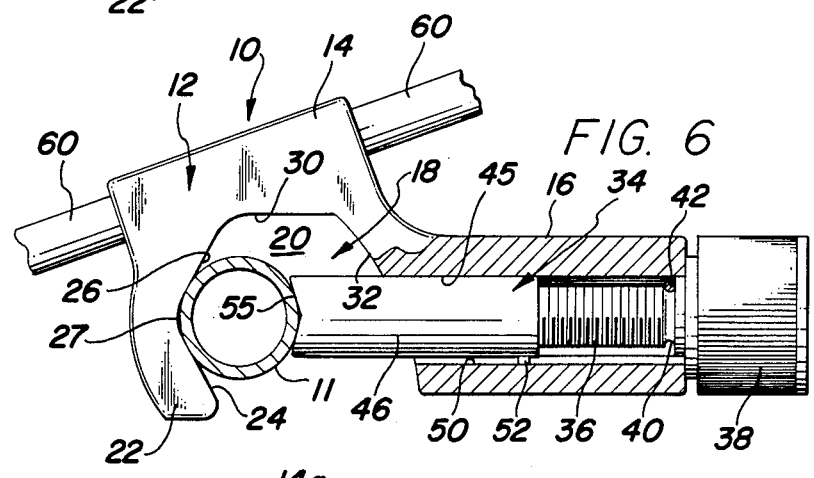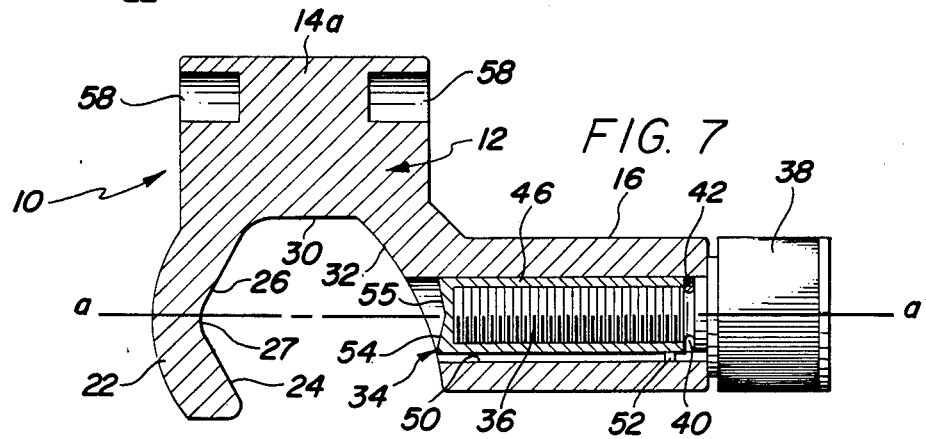

SUPPORT BRACKET

BACKGROUND OF THE INVENTION

This invention relates generally to support brackets, and more particularly to an adjustable support-and-suspension bracket designed for use with I. V. (intravenous) pole systems.

In the medical field, I. V. pole assemblies are commonly employed for many purposes, particularly in hospitals and emergency facilities. An I. V. assembly is basically comprised of a wheeled base member that supports a vertically positioned post having a smaller-diameter telescopic rod mounted therein. The smaller-diameter rod is adjustable vertically for selectively positioning at various heights a pair of fixed, laterally extending, support arms, the height being generally determined by the particular apparatus to be hung thereon, and the function of that apparatus.

Accordingly, I. V. poles are especially designed to support and suspend the different types of bottles or bags containing the various intravenous solutions, the tubes leading therefrom being directly connected to the patient. Often, however, such poles have also been employed to provide a further aid in supporting a wide variety of medical devices that must be positioned adjacent to the patient for specific medical reasons. Since known I. V. poles are limited in their capabilities, makeshift devices are often contrived to assist in supporting the additional equipment. Many times, however, a problem is created when several bottles of solutions must be simultaneously hung or suspended from the pair of arms that extend from the pole. If the I. V. pole is required to be moved, as is often the case, the bottles will invariably make contact with each other, thus causing them to occasionally shake loose or break.

There is also a need to provide a more satisfactory means of suspending primary and secondary I. V. bottles and bags. These containers must be positioned properly, one above the other, in order to promote increased gravity to the secondary I. V. P. B. solutions, so as to facilitate infusion by generating a negative pressure for the primary bottled solutions. This is now accomplished by suspending a four-inch hook member from the horizontal arm which is adapted to support the primary I. V. bottle.

There is a further need for a better means to support all types of urinary-drainage system to the known I. V. poles, particularly during ambulation of the patient, and at the same time maintain the position of the drainage unit below the patient's bladder. The positioning of the drainage unit is very critical so as not to instill contaminated material back to the patient's bladder.

At the present time, there are no known devices that provide atitional appendages, or arm members, compatible for being adjustably secured to available types and models of I. V. pole systems.

SUMMARY AND OBJECTS OF THE INVENTION

The present invention is directed to an adjustable support-and-suspension bracket especially designed to be used with various medical I.V. (intravenous) pole systems, whereby a plurality of I.V. bottles, bags, medical devices, and related apparatuses can be readily supported thereon, so as to overcome the presently known inherent problems that limit or restrict the use of I.V. poles.

Accordingly, the invention has for an important object to provide a new and unique type of adjustable support bracket that is readily compatible with existing pole systems. The bracket is formed with a "C" shaped type clamp-body member and a shaft housing, the clamp-body member being defined by a head member to which support arms are fixedly attached so as to extend longitudinally outward therefrom.

The clamp body further includes an opening therein which is specifically designed to receive various types of mounting structures of suitable configurations. Preferably, the head member is angularly disposed to the shaft housing which is adapted to receive a clamping device that includes a threaded stud secured in the bore of the shaft housing so as to be rotated therein. A clamping sleeve is threadably mounted to the stud and moves longitudinally in and out of the shaft housing by means of a key pin affixed to the clamping sleeve and a keyway formed in the bore. This allows the sleeve to be adjusted to engage any suitable mounting structure positioned within the clamp-body opening.

Another object of the invention is to provide an adjustable support-and-suspension bracket that can be positioned at any suitable location along the I.V. pole, the bracket arms being positioned angularly with respect to the fixed arms of the I.V. pole structure.

Still another object of the invention is to provide a bracket device of this character that allows a plurality of medical devices to be simultaneously hung—such as portable cardiac monitors, in order to assist the nurses and staff in patient care; air humidifiers for respiratory therapy at bedside, thus eliminating the unsatisfactory use of bed rails; enema bags and irrigant devices, which are supported at the recommended position of approximately eighteen inches above the patient while he or she is in a horizontal position; etc.

It is still another object of the invention to provide a device of this character that allows a patient to be ambulatory under various circumstances, such as while being connected to a urinary-drainage system, whereas heretofore the patient or assisting nurse or aide was required to carry the system.

It is a further object of the present invention to provide a bracket of this character that includes relatively few operating parts.

A still further object of the invention is to provide a device of this type that is easy to install, service and maintain.

Still another object of the invention is to provide a device of this character that is relatively inexpensive to manufacture, and is simple yet rugged in construction.

The characteristics and advantages of the invention are further sufficiently referred to in connection with the accompanying drawings, which represent various embodiments. After considering this example, skilled persons will understand that variations may be made without departing from the principles disclosed; and we contemplate the employment of any structures, arrangements or modes of operation that are properly within the scope of the appended claims.

BRIEF DESCRIPTION OF THE DRAWINGS

Other novel features and advantages of the present invention, in addition to those mentioned above, will become apparent to those skilled in the art from a reading of the following detailed description in conjunction with the accompanying drawings, which are presented herein for illustrative purposes only, wherein:

FIG. 1 is a perspective view of the present invention, a support bracket designed to be clamped and mounted to various poles, rails, and other suitable structures;

FIG. 2 is an enlarged, horizontal, cross-sectional view taken substantially along line 2—2 of FIG. 1, but without the lateral support arms mounted thereto;

FIG. 3 is a cross-sectional view taken along line 3—3 of FIG. 2, showing the means for securing the threaded stud for adjusting the clamping sleeve;

FIG. 4 is a perspective view of the clamping sleeve;

FIG. 5 is a top-plan view of the clamp body, with a portion broken away to better shown the position of the clamping sleeve when a larger-diameter structure is clamped therein;

FIG. 6 is a similar view to that of FIG. 5, illustrating the position of the clamping sleeve when it is used to engage a smaller-diameter structure; and FIG. 7 is an alternative arrangement of the present invention wherein the mounting head portion of the clamp body is positioned to allow the support arms to be disposed in a parallel arrangement with the shaft housing.

DESCRIPTION OF THE PREFERRED EMBODIMENT

Referring more particularly to FIG. 1, there is shown a support bracket, generally indicated at 10, which has been specifically designed for use in the medical field to provide a means for attaching various devices to suitable structures, such as I.V. poles. However, it should be understood that the particular arrangement of the support-bracket structure permits the present invention to be employed with structures other than I.V. poles. Such structures include bed rails; crash carts; nursery bassinet frames; instrument tables; and bedside-support diagnostic equipment.

Support bracket 10 comprises a main body structure which will hereinafter be referred to as the clamp body 12. The clamp body is formed with a head member or portion 14 which is angularly disposed relative to the shaft housing member or portion 16. The clamp body 12 further includes a means to receive poles and like structures 11 having various diameters from ¾" to 1¼". The receiving means is so designed that the structure to which the support bracket is mounted need not necessarily have the circular, cross-sectional configuration of a pole. (See FIGS. 5 and 6.)

Hence, the receiving means generally indicated at 18 is defined by an opening 20 having a jaw member 22 which is oppositely disposed and aligned with the stud housing 16, as illustrated in FIGS. 5 and 6. Jaw member 22 is formed with a pair of inclined inner walls 24 and 26 which intersect each other at 27. The intersection point is in direct alignment with the longitudinal axis of the stud housing 16.

Opening 20 is further defined by inner wall 30 and arcuate wall 32. The particular arrangement of walls 24, 26, 30 and 32 permits easy engagement of opening 20 with any suitable structure 11, be it round, square, etc.

Stud housing 16 is formed and adapted to receive and support a clamping means, indicated generally at 34, which comprises a threaded screw stud 36 having a knob member 38. Adjacent the knob there is provided a securing means comprising an annular groove 40 formed in the threaded screw stud 36 and a securing pin 42. The securing pin is fixedly mounted in stud housing 16, as better illustrated in FIG. 3, and is forced into the transverse bore 44 so as to be positioned in annular groove 40. Thus, screw stud 36 is secured in such a manner that it is rotatable around axis a—a but can not move longitudinally within the longitudinal bore 45 formed in stud housing 16.

In order to establish a direct clamping action between structure 11 and the clamping means 34, there is a clamping sleeve 46 threadably mounted to screw stud 36, as seen in FIGS. 2, 3 and 4. Also provided between clamping means 34 and stud housing 16 is a guide means which comprises a longitudinal keyway 50 formed in bore 45 in which a key pin 52 is received. The key pin is fixedly secured to clamping sleeve 46. Hence, as stud 36 is rotated, sleeve 46 will move longitudinally along bore 45—either forwardly or backwardly, depending upon the rotation of knob 38. Clamping sleeve 46 can not rotate with stud 36 because there is a key pin 52 positioned in keyway 50.

Accordingly, in order to position the support bracket about the structure, the clamping sleeve 46 is retracted within bore 45 to allow the particular structure (such as pole 11) to be received in opening 20, whereupon knob 28 is rotated and the clamping sleeve 46 is moved outwardly against the pole, as shown in FIGS. 5 and 6. The free end 54 of clamping sleeve 46 is formed with a vertically arranged groove 55 defined by converging walls. Hence, a pole or rail 11, such as illustrated in FIGS. 5 and 6, will be clamped between jaw member 22 and groove 55, whereby inclined walls 24 and 26 engage the pole on one side and the inclined walls of groove 55 engage the pole on the opposite side.

It should be noted that the guide means provided between clamping means 34 and stud housing 16 may be arranged in reverse of what is herein shown. That is, longitudinal keyway 50 can be formed along the outer longitudinal surface of clamping sleeve 46, the key pin 52 being mounted in stud housing 16 so as to project into bore 45 in order to be received in the keyway of the clamping sleeve.

Thus, a very firm and positive grip is established to secure the bracket and prevent it from moving horizontally or vertically with respect to the pole or any other structure to which it might be attached.

Referring to FIG. 2, head portion or member 14 includes oppositely disposed bores 58. These bores are arranged to receive one or more extension-support arms or members 60, which are fully illustrated in FIG. 1. It should be noted that in the preferred embodiment head portion 14 is angularly positioned relative to axis a—a, as shown in FIG. 2. The angle indicated at "A" may be any suitable degree to allow easy access to knob 38. However, as shown in the alternative arrangement of FIG. 7, head member 14a is shown as being in a parallel plane with the center line a—a.

In order to aid in attaching various devices to support arms 60, each arm is formed with a looped end 62 and a plurality of notches 64. However, the looped ends may be bent so as to project laterally, as illustrated in FIG. 1, or they can be made to extend longitudinally.

The invention and its attendant advantages will be understood from the foregoing description; and it will be apparent that various changes may be made in the form, construction and arrangement of the parts of the invention without departing from the spirit and scope thereof or sacrificing its material advantages, the arrangements hereinbefore described being merely by way of example; and we do not wish to be restricted to the specific forms shown or uses mentioned, except as defined in the accompanying claims.

We claim:

1. A support bracket comprising:
 a body member having a receiving means defined by an opening therein to receive one of several types of support structures on which said support bracket is to be mounted;
 an adjustable clamping means mounted in said body member and positioned for direct engagement with a support structure;
 said clamping means including means for securing said clamping means in said body member; and
 a pair of extension-support arms mounted to said body member and positioned opposite each other, whereby said extension-support arms project outwardly from said body member;
 wherein said body member is formed with a heat portion extending outwardly therefrom, and wherein said extension-support arms are mounted in said head portion so as to be longitudinally aligned with each other and spaced away from said clamping means; and
 wherein said clamping means comprises:
 a threaded screw stud rotatably mounted in said body member;
 a clamping sleeve threadably mounted on said screw stud, wherein said clamping sleeve moves longitudinally along said threaded screw stud as said stud is rotated; and
 guide means positioned within aid body member whereby said clamping sleeve is prevented from rotating within said body member, but said clamping sleeve is allowed to move longitudinally as said threaded screw stud is rotated.

2. A support bracket as recited in claim 1, wherein said opening in said body member is defined by a jaw member formed to engage said support structure as said clamping sleeve engages said support structure.

3. A support bracket as recited in claim 2, wherein said clamping sleeve includes a free end formed with a groove therein for direct engagement with said support structure.

4. A support bracket as recited in claim 3, wherein said jaw member is formed with oppositely disposed, intersecting, inclined walls, the intersection thereof being aligned with said groove of said clamping sleeve, whereby said support structure is clamped therebetween.

5. A support bracket as recited in claim 4, wherein said guide means comprises:
 a guide pin fixedly secured to said clamping sleeve; and
 a keyway formed in said body member to receive said guide pin.

6. A support bracket as recited in claim 4, wherein said body member includes a stud housing having a longitudinal bore formed therein, and wherein said guide means comprises:
 a key pin fixedly secured to said clamping sleeve; and
 a keyway formed in said longitudinal bore to receive said guide pin.

7. A support bracket as recited in claim 6, wherein said threaded screw stud includes a knob, and wherein said securing means comprises:
 an annular groove formed in said threaded screw stud; and
 a securing pin mounted in said body member and positioned to be received in said annular groove, whereby the movement of said threaded screw stud is limited to the rotation thereof.

8. A support bracket as recited in claim 6, wherein said head portion and said extension-support arms are angularly disposed with respect to said stud housing.

9. A support bracket as recited in claim 1, wherein said guide means comprises:
 a keyway; and
 a guide pin;
 said keyway and said guide pin being positioned within said body member for engagement therebetween, whereby said clamping sleeve is restricted from rotational movement within said body member.

10. A support bracket as recited in claim 9, wherein said keyway is formed along the longitudinal surface of said clamping sleeve and said guide pin is mounted in said body member.

11. In combination with a support bracket of the type having a "C"-clamp body member wherein an adjustable clamping means is mounted therein, the improvement which comprises:
 means for securing said clamping means in said body member;
 wherein said clamping means includes a threaded screw stud rotatably mounted in said body member;
 a clamping sleeve threadably mounted on said screw stud;
 wherein said clamping sleeve moved longitudinally along said threaded screw stud as said stud is rotated; and
 guide means positioned within said body member, whereby said clamping sleeve is prevented from rotating within said body member, and whereby said clamping sleeve is allowed to move longitudinally as said threaded screw stud is rotated.

12. The combination as recited in claim 11, wherein guide means comprises:
 a keyway; and
 a guide pin wherein said keyway and said guide pin are located within said body member for engagement with each other, whereby said clamping sleeve is restricted from rotational movement within said body member.

13. The combination as recited in claim 12, wherein said means for securing said clamping means comprises:
 an annular groove formed in said threaded screw stud; and
 a securing pin mounted in said body member and positioned to be received in said annular groove, whereby the movement of said threaded screw is limited to the rotation thereof.

14. The combination as recited in claim 13, wherein at least one support member is attached to said body member.

15. The combination as recited in claim 14, wherein one end of said clamping sleeve is formed having a groove formed therein.

16. The combination as recited in claim 15, wherein said groove is formed having inclined wall-engaging members.

17. An adjustable support-and-suspension bracket adapted to be mounted to a suitable mounting structure, said bracket comprising:

a clamp body having an opening formed therein to receive a mounting structure;

an adjustable clamping means mounted in said clamp body so as to be adjusted for direct engagement with said mounting structure, when said mounting structure is positioned within said opening of said clamp body;

means for securing said adjustable clamping means in said clamp body;

at least one arm member fixedly attached to said clamp body and extending outwardly therefrom; and wherein said adjustable clamping means comprises:

a threaded stud rotatably mounted in said clamp body, said threaded stud including a knob affixed thereto;

a clamping sleeve threadably mounted to said threaded stud, whereby said clamping sleeve moves longitudinally within said clamp body as said threaded stud is rotated; and guide means positioned within said clamp body, whereby said clamping sleeve is prevented from rotating within said clamp body as said clamping sleeve is moved longitudinally relative to said clamp body by said threaded stud.

18. A bracket as recited in claim 17, wherein said clamp body includes:

a head portion extending outwardly therefrom, and wherein said first and second arm members are fixedly mounted to said head portion; and a housing having a longitudinal bore therein to receive said clamping means.

19. A bracket as recited in claim 18, wherein said guide means comprises:

a key pin fixedly mounted to said clamping sleeve; and a keyway formed longitudinally in said bore of said housing, whereby said clamping sleeve is guided along said keyway in a back-and-forth, longitudinal movement as said threaded stud is rotated.

20. A bracket as recited in claim 17, wherein said head portion of said clamp body is angularly disposed with respect to said threaded stud and said clamping sleeve.

21. A bracket as recited in claim 19, wherein said securing means comprises:

an annular groove formed in said threaded stud; and a pin mounted in said housing and positioned so that said pin is received in said annular groove.

* * * * *